United States Patent [19]

Ohno et al.

[11] Patent Number: 4,827,052
[45] Date of Patent: May 2, 1989

[54] OPTICALLY ACTIVE ALCOHOLS

[75] Inventors: Kouji Ohno; Shinichi Saito; Kazutoshi Miyazawa, all of Yokohama; Makoto Ushioda, Kawasaki; Hiromichi Inoue; Naoyuki Yoshida, both of Yokohama, all of Japan

[73] Assignee: Chisso Corporation, Osaka, Japan

[21] Appl. No.: 113,765

[22] Filed: Oct. 28, 1987

[30] Foreign Application Priority Data

Nov. 7, 1986 [JP] Japan ................................. 61-263837
Nov. 17, 1986 [JP] Japan ................................. 61-273590

[51] Int. Cl.$^4$ ............................................. C07C 33/46
[52] U.S. Cl. ..................................... 568/812; 568/809
[58] Field of Search ...................... 568/715, 812, 809

[56] References Cited

U.S. PATENT DOCUMENTS 3,708,544  1/1973  Nordman et al. .................... 568/812

FOREIGN PATENT DOCUMENTS 0016844  1/1984  Japan .................................... 568/812
881588  11/1961  United Kingdom ................ 568/812

Primary Examiner—Werren B. Lone
Attorney, Agent, or Firm—Wenderoth, Lind & Ponack

[57] ABSTRACT

The present invention provided optically active alcohols represented by the general formula:

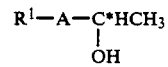

wherein $R^1$ indicates an alkyl or alkyloxy group having a carbon number of 1–18, and A indicates a phenyl or a biphenyl group; or a phenyl or biphenyl group having a halogen atom or a cyano group. The alcohols are intermediates of optically active materials useful for components of liquid crystal materials for liquid crystal display elements having quick response.

7 Claims, No Drawings

OPTICALLY ACTIVE ALCOHOLS

BACKGROUND OF THE INVENTION

The present invention relates to new optically active alcohols which are intermediates of optically active materials useful for components of liquid crystal materials for liquid crystal display elements.

Display element of a twisted nematic (TN) type is widely used as a liquid crystal display element. The liquid crystal display is characterized in less eyestrain and minimized consumption of electric power because it is a non-emissive type. However, the display element of the TN type has an unsolved disadvantage in which the response is slower than that of a display element of light emitting type (e.g. an electroluminescence display, a plasma display and the like). The improvement of the response time of the liquid crystal display is tried in many ways. As a liquid crystal display using a different principle instead of the TN type display, a display method using a ferroelectric liquid crystal is reported by N. A. Clark et al. (ref. Appl. Phys. Lett. 36, 899 (1980)).

This display method utilizes a chiral smectic C phase (abbreviated as $S_C^*$ phase hereinafter) or a chiral smectic H phase (abbreviated as $S_H^*$ phase hereinafter) of ferroelectric liquid crystals, and it has three excellent characteristics in comparison with the TN display method. The first characteristic is quick response and the response time is less than 1/100 of that of the TN display element. The second characteristic is that the method has memory effect and it facilitates multiplexed drive in cooperation with the quick response. The third charateristic is to obtain easily its gray scale. There are problems of temperature dependence of threshold voltage, electric voltage dependence of response speed and the like because applied voltage is controlled for obtaining the gray scale in the TN method. In comparison with the TN method, the display method applying the light switch effect of the $S_C^*$ phase is suitable for graphic display because it is able to obtain the gray scale by controlling inversion time of polarity.

For such materials of ferroelectric liquid crystals having excellent characteristics, liquid crystal compounds having the $S_C^*$ phase and the high valve spontaneous polarization (abbreviated as Ps hereinafter) were desired. Afterward, it was found that a ferroelectric liquid crystal mixture was obtained by adding a chiral and optically active compound, which does not show a liquid crystal phase by itself, to a smectic liquid crystal. Thus, search fields of the materials of ferroelectric liquid crystals were more widened (ref. Mol. Cryst. Liq. Cryst. 89, 327 (1982)).

It is considered that molecular structures of such optically active compounds are preferably nearly stick-like cylinders, and core structures linking at least two six-membered rings by any linkage of ester linkage, ethane linkage, covalent linkage, etc. are desirable.

SUMMARY OF THE INVENTION

Accordingly, an object of the present invention is to provide new optically active alcohols which are useful for intermediates or precursors of optically active materials suited for components of liquid crystal materials.

The present invention is:

(1) An optically active alcohol represented by the general formula:

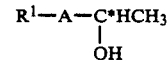

wherein $R^1$ indicates an alkyl or an alkyloxy group having a carbon number of 1-18, A indicates

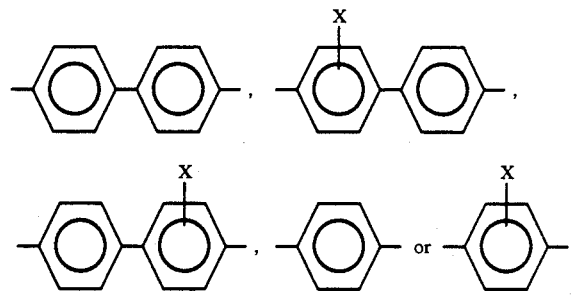

and X indicates a halogen atom or a cyano group.

Furthermore, the features are shown in the following (2) and (3).

(2) An optically active alcohol as mentioned above (1) represented by a general formula:

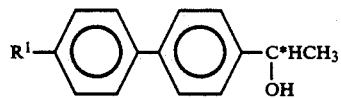

wherein $R^1$ indicates an alkyl or an alkyloxy group having a carbon number of 1-18.

(3) An optically active alcohol as mentioned above (1) represented by a general formula:

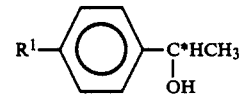

wherein $R^1$ indicates an alkyl or an alkyloxy group having a carbon number of 1-18.

DESCRIPTION OF PREFERRED EMBODIMENTS

Materials provided by the present invention are optically active 1-(4-alkylbiphenyl-4'-yl)ethanol, 1-(4-alkyloxybiphenyl-4'-yl)ethanol, 1-(4-alkylphenyl)ethanol, 1-(4-alkyloxyphenyl)ethanol and an optically active compounds which is substituted by a halogen atom or a cyano group at one of lateral positions of these phenylene rings.

The following optically active alcohols such as 1-(4-pentylbiphenyl-4'-yl)ethanol, 1-(4-octyloxybiphenyl-4'-yl)ethanol, 1-(4-octylphenyl)ethanol, 1-(4-heptyloxyphenyl)ethanol, 1-(3-fluoro-4-octyloxybiphenyl-4'-yl)ethanol are exemplified.

The method for preparing the optically active alcohols of the present invention is described hereinafter.

The optically alcohols of the present invention can be optically resolved by biochemical asymmetric transesterification or asymmetric ester synthesis from commercially available racemic alcohols or racemic alcohols which are synthesized by the following equation:

(A case wherein R¹ of formula (I) is an alkyl group)

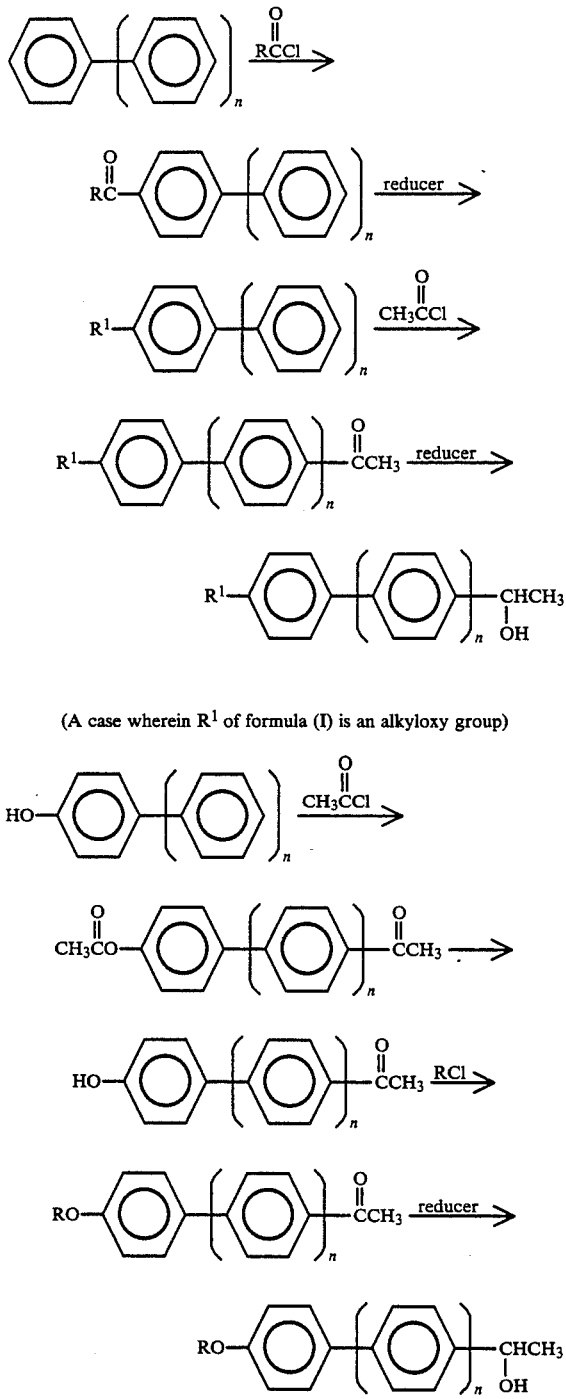

(A case wherein R¹ of formula (I) is an alkyloxy group)

wherein n is 0 or 1, and R indicates an alkyl group.

Racemic alcohols of formula (I) wherein one of lateral hydrogens of phenylene rings is substituted by a halogen atom or a cyano group, can be prepared by the same method as described above.

When the optical resolution is conducted by the transesterification, a racemic alcohol and a triglyceride such as tributyrin are suitably reacted in a liquid phase in the substantial absence of water at 30°–45° C. by adding an enzyme such as lipase. An enzyme on market can be used. When the mixture of triglyceride and the racemic alcohol can not form a liquid phase, a solvent of hydrocarbon such as heptane, toluene, etc., can be used in the reaction. The reaction time is about one to several ten days. After the reaction, the enzyme is separated and the produced ester and unreacted alcohol are separated from the filtrate by the separation means such as distillation, chromatography and the like. The separated alcohol is one of the pair of antipodes, and the other antipodal optically active alcohol is obtained by the hydrolysis of the produced ester.

The optically active ester can be prepared from the optically resolved alcohol of formula (I) and the fatty acid having a carbon number of 2–19. The obtained ester is dissolved in smectic liquid crystals, and a smectic mixture having a great value of spontaneous polarization (Ps) can be obtained. As an example, although (−)-4-octyloxy-4'-(1-hexanoyloxyethyl)biphenyl which is obtained by the reaction of (−)-1-(4-octyloxybiphenyl-4'-yl)ethanol and caproic acid does not show a liquid crystal phase by itself, it can be added to smectic C liquid crystals and a ferroelectric liquid crystal mixture can be obtained.

By using the ferroelectric liquid crystal mixtures as the materials of light switch elements, it is able to obtain the liquid crystal displays having quick response.

The following examples illustrate the present invention more specifically. The following application example also illustrates the usefulness of the optically active alcohols of the present invention.

EXAMPLE 1

Ten grammes of enzyme (produced by Amano Pharmaceutical Co. Ltd., lipase "Amano" P), 9.0 g (35 mmol) of (±)-1-(4-pentylbiphenyl-4'-yl)ethanol and 15.9 g (52.5 mmol) of tributyrin were dissolved in a mixed solvent of 100 ml of heptane and 50 ml of toluene and the mixture was charged into three-necked flask and stirred for 15 days at 35° C. After the reaction was stopped, the enzyme was removed by filtration and the filtrate was concentrated. The residue was chromatographed over silica gel, and the desired compounds were isolated, respectively. As the result, 2.6 g of (−)-1-(4-pentylbiphenyl-4'-yl)ethanol (yield: 29%, m.p. 83.8° C., $[\alpha]_D$ −25.0° (c 1.0, $CH_3OH$)) and 2.5 g of (+)-4-(1-butanoyloxyethyl)4'-pentylbiphenyl (yield: 22%, m.p. 38.1° C., $[\alpha]_D$ +96.4° (c 1.0, $CH_3OH$)) were obtained, respectively.

EXAMPLE 2

Using the same method as in Example 1, (±)-1-(4-octyloxybiphenyl-4'-yl)ethanol was used as a starting material, (−)-1-(4-octyloxybiphenyl-4'-yl)ethanol (m.p. 123.6° C., $[\alpha]_D$ −27.0° (c 1.0, $CHCl_3$)) and (+)-4-octyloxy-4'-(1-butanoyloxyethyl)biphenyl (m.p. 56.9° C., $[\alpha]_D$ +94.0° (c 0.1, $CH_3OH$)) were obtained, respectively.

EXAMPLE 3

Using the same method as in Example 1, (±)-1-(4-heptyloxyphenyl)ethanol was used as a starting material, (−)-1-(4-heptyloxyphenyl)ethanol ($[\alpha]_D$ −14.4° (c 1.0, $CH_3OH$)) and (+)-1-(4-heptyloxyphenyl)ethyl butyrate were obtained. Further, this ethyl butyrate was hydrolyzed, and (+)-1-(4-heptyloxyphenyl)ethanol (m.p. 36.7° C., $[\alpha]_D$ +24.9° (c 1.0, $CH_3OH$)) was obtained.

EXAMPLE 4

Using the same method as in Example 1, (±)-1-(heptylphenyl)ethanol was used as a starting material, (−)-1-(heptylphenyl)ethanol ($[\alpha]_D^{24.1}$ −13.4° (neat)) and (+)-1-(heptylphenyl)ethanol ($[\alpha]_D^{24.1}$ +27.6° (neat)) were obtained.

APPLICATION EXAMPLE

Seven grammes (21 mmol) of (−)-1-(4-octyloxybiphenyl-4'-yl)ethanol prepared in Example 2, 7.5 g (36 mmol) of N,N'-dicyclohexylcarbodiimide and 1.0 g of 4-dimethylaminopyridine were dissolved in 200 ml of dichloromethane. To the solution, 3.4 g (29 mmol) of caproic acid was added and the mixture was stirred for six hours at room temperatre. The deposit crystals were filtered, 200 ml of water was added to the filtrate, and the organic layer was separated. 6N hydrochloric acid was added to the organic solution, and then the solution was neutralized with the aqueous solution of 2N sodium hydroxide. The neutralized solution was washed with water until the washed water became neutral. The solvent and low-boiling fractions were distilled off from the obtained solution. The residue was recrystallized from ethanol and the desired (−)-4-octyloxy-4'-(1-hexanoyloxyethyl)biphenyl 6.8 g was obtained. m.p. 60.8° C., $[\alpha]_D$ −78.4° (c 0.88, C$_2$H$_5$OH).

Ten parts by weight of the obtained (−)-4-octyloxy-4'-(1-hexanoyloxyethyl)biphenyl was added to 90 parts by weight of following smectic C liquid crystal mixture (A) to prepare a liquid crystal mixture (B).

Liquid crystal mixture (A) consists of the following:

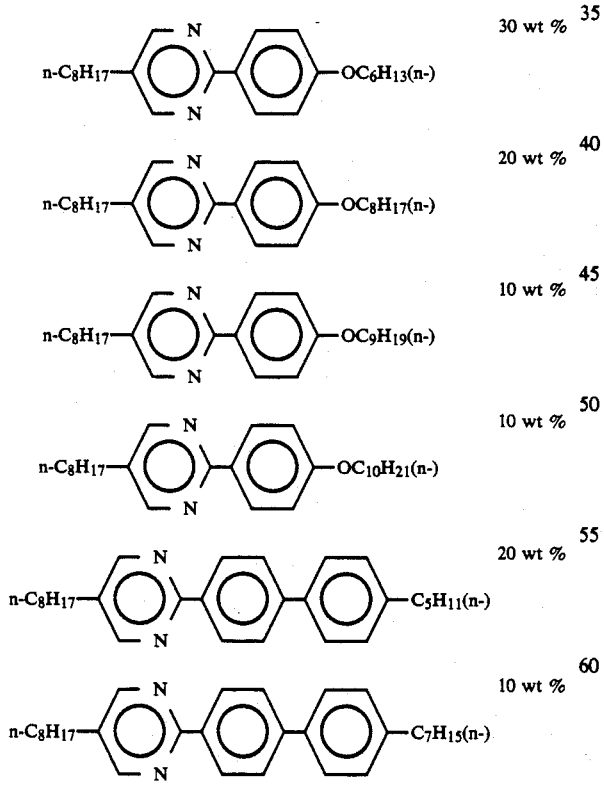

and its phase transition temperatures were represented as the following:

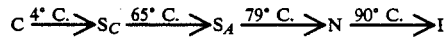

wherein C, S$_C$, S$_A$, N and I indicate a crystal phase, a smectic C phase, a smectic A phase, a nematic phase and an isotropic liquid phase, respectively. No spontaneous polarization was produced by the mixture.

Liquid crystal mixture (B) showed the chiral smectic C phase at temperatures of 2° C.–37° C., the value of spontaneous polarization was 4.4nC/cm$^2$ at 25° C. and the tilt angle was 12°.

Further, mixture (B) was sealed in a cell 2 μm in thickness having transparent electrodes obtained by homogeneous aligning treatment, in which polyvinylalcohol of the aligning agent was applied to the surfaces of the electrodes and the surfaces were rubbed. The resulting cell of liquid crystals was placed between two crossed polarizing plates and 10 V of peak value of square waves was applied to the cell. Then, the change of transmittance of light was observed. The response time of this liquid crystal cell was determined by the change of transmittance light was 100 μsec. at 25° C.

We claim:

1. An optically active alcohol represented by the general formula:

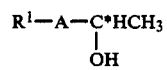

wherein R$^1$ indicates an alkyl or alkyloxy group having a carbon number of 1-18, A indicates

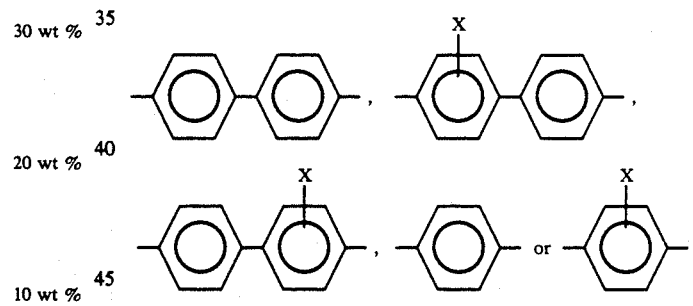

and X indicates a halogen atom or a cyano group.

2. An optically active alcohol as claimed in claim 1, wherein the alcohol is represented by the general formula:

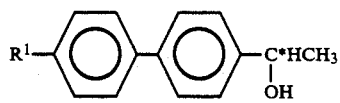

wherein R$^1$ indicates an alkyl or alkyloxy group having a carbon number of 1-18.

3. An optically active alcohol as claimed in claim 1, wherein the alcohol is represented by the general formula:

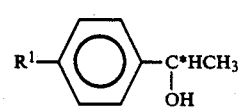

wherein $R^1$ indicates an alkyl or alkyloxy group having a carbon number of 1–18.

5. An optically active alcohol as claimed in claim 1, wherein $R^1$ is a pentyl group and A is a biphenyl-4,4'-diyl group.

5. An optically active alcohol as claimed in claim 1, wherein $R^1$ is a octyloxy group and A is a biphenyl-4,4'-diyl group.

6. An optically active alcohol as claimed in claim 1, wherein $R^1$ is a heptyloxy group and A is a 1,4-phenylene group.

7. An optically active alcohol as claimed in claim 1, wherein $R^1$ is a heptyl group and A is a 1,4-phenylene group.

* * * * *